(12) United States Patent
Goldstein

(10) Patent No.: US 10,286,223 B2
(45) Date of Patent: May 14, 2019

(54) INDUCTION COIL FOR LOW RADIO FREQUENCY APPLICATIONS IN A HUMAN HEAD

(71) Applicant: AMF Lifesystems, LLC, Auburn Hills, MI (US)

(72) Inventor: Robert C. Goldstein, Grand Blanc, MI (US)

(73) Assignee: AMF LIFESYSTEMS, LLC, Auburn Hills, MI (US)

( * ) Notice: Subject to any disclaimer, the term of this patent is extended or adjusted under 35 U.S.C. 154(b) by 118 days.

(21) Appl. No.: 15/599,740

(22) Filed: May 19, 2017

(65) Prior Publication Data

US 2017/0333726 A1    Nov. 23, 2017

Related U.S. Application Data

(60) Provisional application No. 62/339,679, filed on May 20, 2016.

(51) Int. Cl.

| | |
|---|---|
| *A61N 2/00* | (2006.01) |
| *A61N 2/02* | (2006.01) |
| *H05B 6/10* | (2006.01) |
| *H05B 6/44* | (2006.01) |
| *A61B 18/04* | (2006.01) |
| *A61B 18/00* | (2006.01) |
| *A61N 1/40* | (2006.01) |

(52) U.S. Cl.
CPC ............... *A61N 2/02* (2013.01); *A61B 18/04* (2013.01); *A61N 2/004* (2013.01); *H05B 6/106* (2013.01); *H05B 6/44* (2013.01); *A61B 2018/00446* (2013.01); *A61B 2018/00577* (2013.01); *A61N 1/406* (2013.01); *H05B 2214/04* (2013.01)

(58) Field of Classification Search
CPC ... A61N 2/00; A61N 2/02; A61N 1/40; H05B 6/00; H05B 6/02; H05B 6/105
USPC ........................ 600/9–15; 607/103, 105, 113
See application file for complete search history.

(56) References Cited

U.S. PATENT DOCUMENTS 6,575,893 B2    6/2003   Feucht

OTHER PUBLICATIONS

Treatment of Malignant Gliomas with Interstitial Irradiation and Hyperthermia; Int. J. Radiation Oncology Biol. Phys; vol. 24, pp. 657-667; 1992.
Pratical Induction Heating Coit Designs for Clinical Hyperthermia with Ferromagnetic Implants, P.R. Stauffer IEEE Transactions on Biomedical Engineering, vol. 41, No. 1, Jan. 1994.
Improved Tissue Cryopreservation Using Inductive Heating of Magnetic Nanoparticles; Science Translational Medicine, vol. 9, Issue 379, eaah4586 Mar. 1, 2017, Navid Manuchehrabadi et al.
(Continued)

*Primary Examiner* — John P Lacyk
(74) *Attorney, Agent, or Firm* — Fishman Stewart PLLC

(57) ABSTRACT

An induction coil and method for heating susceptors within a portion of a living body, include an effective diameter that is determined based on a cross-sectional area of the induction coil, a length determined along an axis of the induction coil that is orthogonal to the cross-sectional area, and a ratio of the length to the effective diameter that ranges between 0.25 and 0.75, such that a magnetic field is generated that ranges between 1 kA/m and 40 kA/m with an input frequency that ranges between 50 kHz and 1 MHz.

20 Claims, 11 Drawing Sheets

(56) References Cited

OTHER PUBLICATIONS

Scutti, Susan. "Will We Be Able to Cryogenically Freeze Organs One Day?" *CNN*, Cable News Network, Mar. 6, 2017, www.cnn.com/2017/03/01/health/freezing-organ-donation-nanoparticle-warming-study.

Scharpling, Nathaniel. "With Iron Nanoparticles, Cryopreserved Tissue Springs Back to Life." *D-Brief*, Mar. 1, 2017, blogs.discovermagazine.com/d-brief/2017/03/01/cryopreservation-tissue-organ-preservation/.

Jordan, Andreas, et al. "Magnetic Nanoparticles for Cancer Therapy." *Physics of Thermal Therapy: Fundamentals and Clinical Applications*, by Eduardo Moros, CRC Press, 2012, pp. 293-318.

INDUCTION COIL FOR LOW RADIO FREQUENCY APPLICATIONS IN A HUMAN HEAD

CROSS-REFERENCE TO RELATED APPLICATIONS

This application claims priority to U.S. Provisional Patent Application No. 62/339,679, filed on May 20, 2016, the contents of which are hereby incorporated by reference in their entirety.

TECHNICAL FIELD

The disclosure relates to an induction coil for the generation of and control of magnetic fields in a human head in the low radio frequency ("RF") range for applications such as magnetic fluid hyperthermia, RF hyperthermia, thermal ablation, and wireless magnetothermal deep brain stimulation.

BACKGROUND

The use of alternating magnetic fields in the low radio frequency range may be a possible technique to use when selective heating of bodies with low equivalent electrical conductivity is desired. Selective heating in these bodies may be achieved by placing a susceptor, or in most cases a group of susceptors, in the area where heating is desired. Mechanisms to undertake the possible technique may include, but are not limited to, magnetic fluid hyperthermia, RF hyperthermia, magnetic hyperthermia, plastic welding with embedded magnetic bodies, die heating with embedded magnetic bodies, wireless magnetothermal deep brain stimulation, and thermal ablation. In the past, the possible technique has had limited success due to the inability to generate appropriately robust magnetic fields in sufficiently large volumetric regions and at the proper frequency to generate sufficient heating in the desired areas of a body to produce desired technological effects. In the case of living bodies, a desired technological effect may include a therapeutic effect.

SUMMARY

An induction coil connected to a heat station is fed by a power source. The induction coil geometry is oval in its construction, in one example, and optimized to minimize magnetic energy used to generate a magnetic field, while providing the ability to maximize differential heating between disparate regions (e.g., regions where heating is desired and regions where heating is undesirable). The induction coil may also utilize a single turn or possibly two turns (depending upon the desired magnetic field strength) to reduce the voltage, which in turn reduces the potential for an electrical break, as well as electrical fields a patient will be exposed to.

DETAILED DESCRIPTION

Figure 1A:
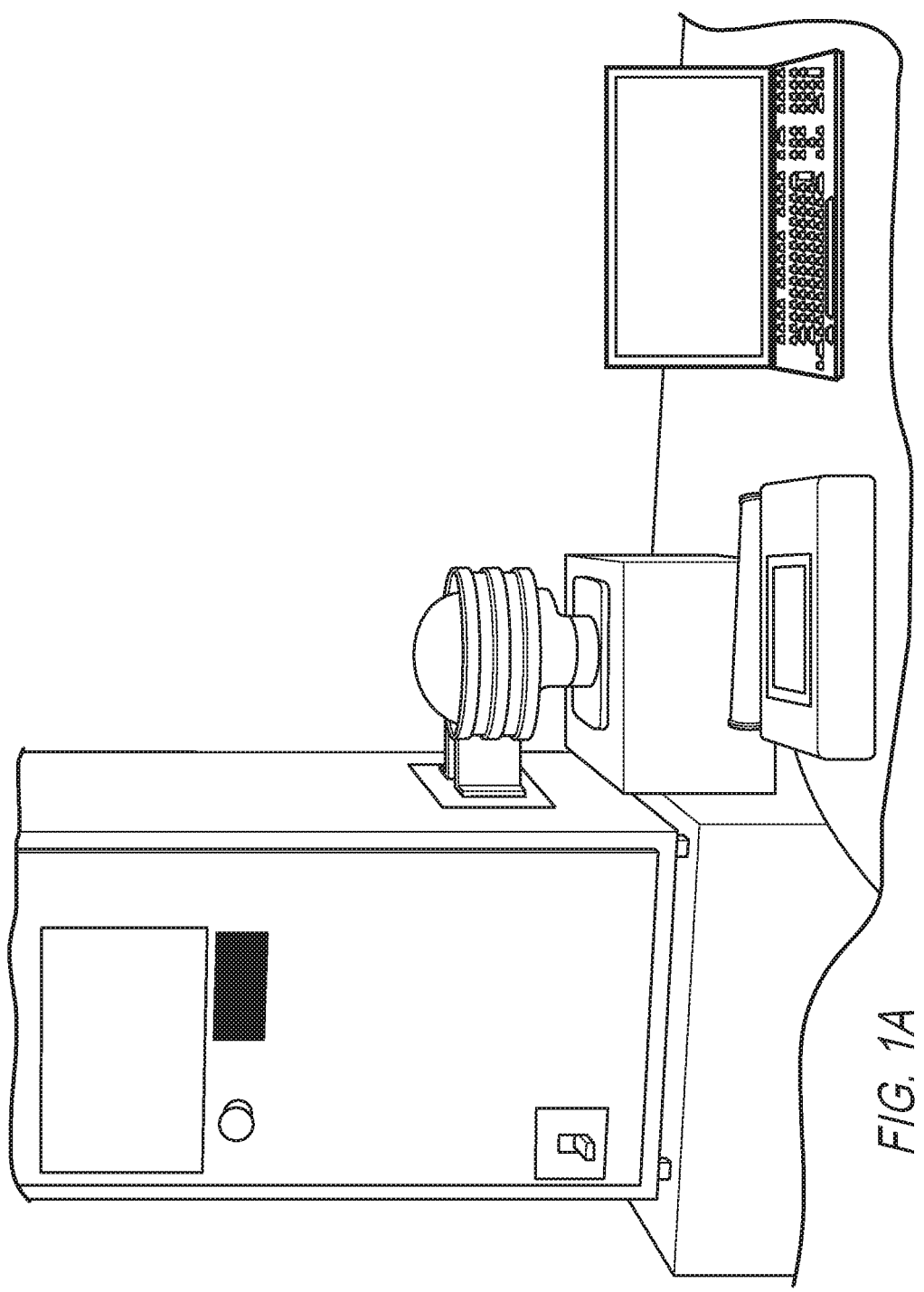
FIG. 1A illustrates an exemplary oval induction coil for use with an induction system. In the illustration a body in the form of a human head is shown received in the interior of the coil.

An induction coil, which can have many configurations, carries an alternating frequency current. The current generates an alternating magnetic field within a volume that is interior to and surrounded by the coil, which in turn induces eddy currents in electrically conductive bodies positioned within the volume and causing heating of magnetic bodies (a combination of eddy currents, hysteresis, Neal heating, Brownian heating, etc., depending upon the characteristics of the magnetic body) that are positioned in the volume and exposed to the alternating magnetic field. The amount of eddy current heating depends upon the shape of the induction coil, the strength and frequency of alternating magnetic field, the shape of the conductive body, the orientation of the conductive body relative to the magnetic field, and the electrical and magnetic properties of the electrically conductive body, as examples. Controlled, selective heating is the desirable outcome of the magnetic field exposure, and may be used applying magnetic fields to a body such as a human head. And, although the following discussion pertains particularly to treatment of a tumor in a human head (having susceptors therein, such as magnetic nanoparticles, thermoseeds, or other metallic inserts), it is contemplated that the disclosure is applicable to treating susceptors positioned anywhere within a human body, such as in a torso, a limb, or an extremity, as examples. In addition, it is also contemplated that the disclosure is not limited to use in a human patient, but may be used in any animal where it may be desirable to heat susceptors for treatment of, for instance a tumor.

In addition to eddy currents, the alternating magnetic field causes hysteretic heating in magnetic bodies exposed to it. The distribution of hysteretic heating depends upon the shape of the induction coil, the level of alternating magnetic field, the orientation of the magnetic field relative to the magnetic body, the concentration of the magnetic bodies in an area, and the magnetic properties of the bodies. Controlled, selective heating is the desirable outcome of the magnetic field exposure for some thermal ablation and some magnetic fluid hyperthermia applications.

For very small magnetic bodies, such as magnetic nanoparticles, the amount of power that they absorb when exposed to an alternating magnetic field may not match well to traditional models for heating of larger magnetic bodies as it has varying contributions from different heating mechanisms. New models for describing this behavior have been proposed, but additional work is ongoing. Experiments remain the most reliable method for characterization of heating of nanoparticles in an alternating magnetic field. The amount of heat per gram of magnetic material in these very small bodies is referred to as the Specific Absorption Rate, or SAR, in the field of magnetic fluid hyperthermia. Some researchers use the term Normalized Power Loss (NPL) or Specific Loss Power (SLP) to describe the power absorption characteristics of the particles. For consistency, the term SAR is used in this document. The SAR and resulting heating effect in magnetic fluid hyperthermia applications depends upon the shape of the induction coil, the level and frequency of alternating magnetic field, the orientation of the magnetic field relative to the magnetic body, the size of the magnetic bodies, the concentration of the magnetic bodies in an area, and the magnetic properties of the bodies, as examples. Controlled, selected heating of these very small magnetic bodies is the desirable outcome of the magnetic field exposure for some thermal ablation and some magnetic fluid hyperthermia applications.

Over the past few decades, there have been several successful in-vitro and in-vivo small animal studies (mouse and rat) performed using magnetic fluid hyperthermia for the purpose of cancer treatment. In Europe, the technology has been used in combination with radiation to extend the life of patients with glioblastoma multiforme (GBM) by 6-12 months. These studies have shown that non-toxic concentrations of iron oxide particles coated with dextran or other biologically compatible components are exposed to magnetic fields with strengths of 1 kA/m to around 100 kA/m at frequencies of 50-400 kHz over periods from several seconds to hours produced sufficient temperature rises in tumors or cancer cells relative to the healthy surrounding tissues to produce a therapeutic effect. The particles were delivered to the tumor either by direct injection or were antibody guided. The elevated tumor temperatures resulted in tumor growth rate decline, tumor shrinkage, complete tumor cessation, or significant sensitization of the tumor tissue to subsequent radiation or other complimentary treatment. The side effects of the successful treatments were significantly less than for alternative methods.

In the hyperthermia field, thermal dosimetry is evaluated using a method that normalizes a time-temperature curve to an equivalent time at 43 C. This equation uses the temperature exceeded by 90% of the tumor volume ($T_{90}$) and the time (t) spent at the elevated temperature to calculate the cumulative equivalent minutes at 43 C (CEM43). The formula for CEM 43 is:

$$CEM43 = t\, R^{43-T90}; \qquad \text{Eqn. 1.}$$

In equation 1, R is a constant with a value that depends upon the temperature achieved. If $T_{90}$ is below 43, the value for R is 0.25. If $T_{90}$ is above 43, the value for R is 0.5. The larger the CEM43 is, the greater the effect that the hyperthermia treatment will have on the tumor.

For treatment of deep seated tumors in a human head, these strong magnetic fields are generated in a relatively large volume. For instance, a system used to treat GBM in Europe utilizes a transverse flux induction coil design with movable poles. The system is designed to accommodate treatment of cancer anywhere in the body. The downside of this flexibility is that it puts out a wide distribution of the magnetic field to achieve the desired magnetic field in the targeted area. This wide distribution of magnetic field leads to higher levels of unintended heating of surrounding tissue (or metallic implants in adjacent body regions) and a larger corresponding power supply and heat station for the same heating effect. The result is that the device is limited in the amount of heating that it can generate in the targeted areas, resulting in limited effectiveness of the device. That is, by placing an upper limit on the maximum temperature that occurs in the unintended region (to avoid damage to healthy tissue, for instance), the amount of heating in the intended region is thereby limited. More specifically, known devices result in a magnetic field gradient that extends well into regions of healthy tissue, causing eddy current heating in undesirable locations.

In a low radio frequency range (50-400 kHz), efficiency of heating of the human body lying flat between a two pole transverse flux-style induction coil will be higher than if the magnetic field were to be oriented in the longitudinal direction over the same volume. This is highly undesirable and limits the ability to selectively heat the targeted region.

Therefore, a longitudinal flux induction heating coil is a disclosed design for magnetic hyperthermia applications. For longitudinal flux induction coils, the magnetic field strength is concentrated inside of the induction coil cross-section and quickly declines outside of the length of the induction coil and outside of the outer diameter. The active power at a given frequency and magnetic field strength (ignoring any power losses the human body) is proportional to the internal surface area of the induction coil. Induction heating power supplies for this frequency range are capable of delivering several kilowatts to over a megawatt if properly tuned and conditioned. These power supplies may be modified to meet the needs of the magnetic fluid hyperthermia industry.

The reactive power that may be associated with the magnetic field for longitudinal flux induction coils is generally approximately proportional to the volume inside of the induction coil. This means that reactive powers will be several hundred kVAR up to potentially over 10 MVAR. This level of reactive power creates challenges for the design of heat stations due to the available components. Film based capacitors, for instance, are limited in voltage, and ceramic based capacitors are limited in current. Minimizing the reactive power through the induction coil design will be beneficial in reducing the complexity and cost of the heat station. Also, reducing the total magnetic energy passing through the center of the induction coil will result in lower unintended heating of the patient by eddy currents.

In view of the foregoing, it would be desirable to provide an induction coil that produces a magnetic field that is longitudinal to the head and that is customized to contour to a shape similar to that of the human head for medical therapies in the head. This will minimize the internal cross-section of the induction coil to minimize the reactive and active power. Also, the length of the induction coil may be optimized to maximize temperature in the tumor relative to the surrounding healthy tissue based upon the target heating size and duration of treatment.

Figure 1B:
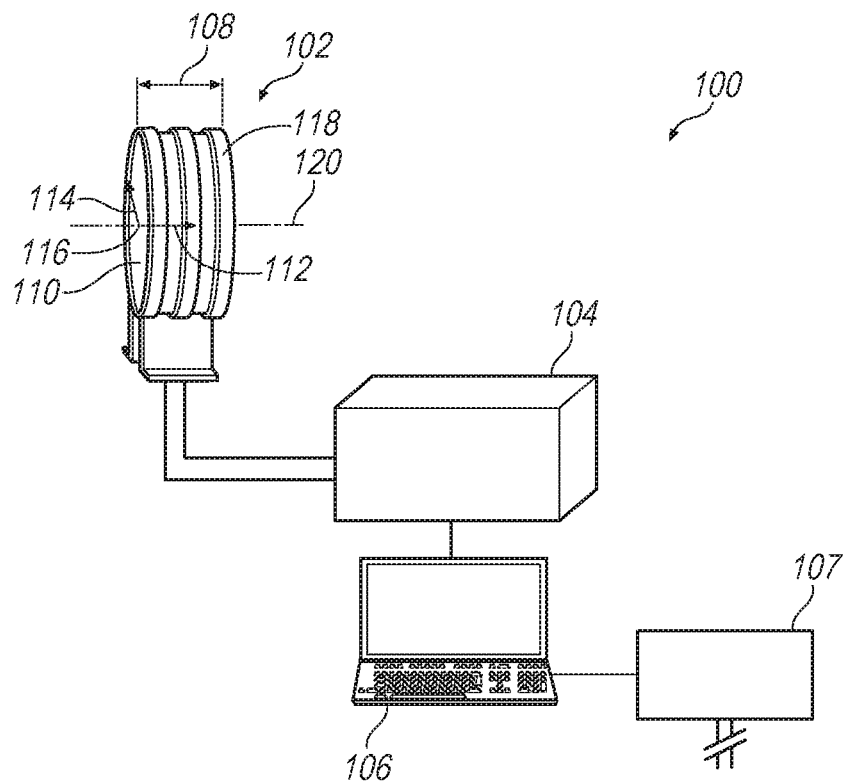
FIG. 1B is a schematic system having a coil in perspective view, with power supply and controller.
Figure 1C:
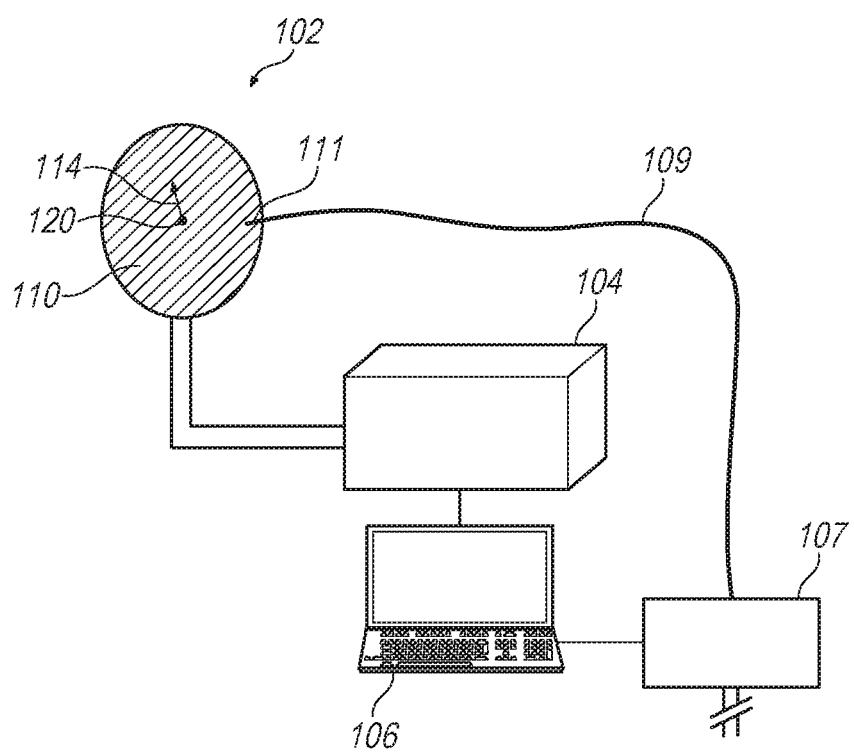
FIG. 1C is a schematic system having a coil in plan view, with power supply and controller.

The above features are addressed using an oval induction coil similar to that shown in FIGS. 1A and 1B for exemplary purposes. FIG. 1A shows aspects of an exemplary oval induction coil, and FIG. 1B shows a schematic of a system 100 for treatment of GBM according to one example. FIG. 1B shows system 100 in a perspective view that includes a single turn coil 102, an AC power supply 104, an optional computer/controller 106, and a temperature monitoring device 107. FIG. 1C shows a schematic of system 100, showing coil 102 in a plan view. Coil 102, although illustrated as a single coil, may have two, or more than two, coils that wrap in a circumferential direction of coil 102, as will be further discussed. Further, although an oval coil is illustrated, it is contemplated that coil 102 may be in other shapes as well. For instance, coil 102 may be circular in shape, in which case coil 102 may be formed as a cylinder. In addition, although an oval is contemplated and illustrated in the figures, performance comparisons between an oval geometry and a circular (or cylindrical) geometry are comparable and result in the same benefits and improved thermal performance. Further, FIG. 1C also illustrates a temperature monitoring device 107, and in the illustration a temperature sensor 109 is shown having its end 111 positioned within a cross-sectional area 110 thereof. Temperature sensor 109 may be a thermocouple or other known device that may output either an analog or digital signal that corresponds with a temperature or temperature change. As such, end 111 is positionable within, for instance, a human head, during treatment to measure a temperature within the human head (or more generally within a region being treated), as is common within the art. Also, although only one temperature monitoring device 107 is shown, it is contemplated that two or more temperature sensors may be coupled to temperature monitoring device 107 to provide temperature at multiple points. Accordingly, thermal models illustrated herein are conducted using a 2-dimensional axisymmetric thermal model, which generally represents the coil as a cylinder, and the results illustrated herein are equally applicable to an oval-shaped coil as well.

Coil 102 includes a length 108 and cross-sectional area 110 that, in the illustrated example, is oval in shape. In such fashion, and as shown in FIG. 1A, coil 102 may be positioned over a human head and along an axial or longitudinal direction thereof, as shown by axial direction 112 of FIG. 1B. In general, a body part such as a head is positioned within the coil (the orientation of which can be seen in FIG. 1A), such that a small clearance of a few millimeters to up to several centimeters is formed between the head and coil 102. The tumor center is centered axially within coil 102 such that magnetic fields formed within the head are approximately uniform in a tumor volume and about a central axis of the head (extending approximately along a direction of the spine). Coil 102 also includes a radial direction 114 which, because of the oval cross-section of coil 102, varies as a function of the radial direction 114 about an axial and radial center 116, itself centered at an axial center 118 of coil 102. As stated, however, coil 102 may be shaped in a circular shape, in which case clearance between coil 102 and a head positioned therein (not shown) may vary as a function of circumferential direction. An oval shaped coil may be positionable with approximately uniform clearance between the head and the coil, while a circular shaped coil may have increased gaps in comparison, with minimal differences in field strength distribution compared to the oval shaped coil. Nevertheless, the disclosed coil 102 generates a relatively uniform distribution in a given treatment volume, but non-uniform in the head overall of magnetic field strength that may be applied to a tumor volume by placement of a head within coil 102, and the criteria for selection of whether circular or oval may be based on other factors such as cost of fabrication or the age of the patient being treated (such as an infant versus an adult, as an example).

If circular in design, the diameter of the coil is determined simply based on a diameter of the coil as seen in its plan view. However, in a non-circular cross-section (i.e., an oval in this example), an effective diameter for coil 102 is determined based on cross-sectional area 110 of the coil 102. Thus, in the example provided, the illustrated cross-sectional area 110 is an oval, but it is contemplated that any cross-sectional shape may be considered such as a circular cross-section. However, for more complicated cross-sectional shapes (i.e., non-oval and non-circular), to first order and in order to determine the length/diameter, the effective diameter may be calculated as if the cross-sectional area were a circle and therefore having a uniform diameter, as one example (in which case the coil would be cylindrical in shape). Thus, the effective diameter ($D_{effective}$) is a square root of four times a ratio of the cross-sectional area (Area) divided by π That is:

$$D_{effective} = \sqrt{\frac{4 \times \text{Area}}{\pi}};  \quad \text{Eqn. 2.}$$

Regardless, coil 102 includes a cross-sectional area 110 that is sufficient to pass over a human head such that the human head is positionable along axis 120 of the coil 102.

Length 108 of coil 102 is determined along an axis 120 that is orthogonal to the cross-sectional area 110. According to the disclosure, a ratio of length 108 to the effective diameter ranges between 0.25 and 0.75. Thus, a magnetic field is generated that ranges between 1 kA/m and 40 kA/m with an input frequency that ranges between 50 kHz and 1 MHz from power supply 104.

The disclosed induction coil could be used for treating of areas of up to several centimeters in length and, in one example, 6 cm long located anywhere in the head. However, it is contemplated that the coils disclosed may be used for treating larger tumors or multiple tumors in different locations by axially moving the coil during treatment or between sequential treatments. Thus, in an example in which a 6 cm treatment is applied, tumors of much greater length or lengths of the body where multiple tumors occur, such as 9 cm, 12 cm, or greater may be treated by either moving the patient in an axial direction within the coil, or by moving the coil axially about the patient.

Due to the efficiency of the induction coil, this relatively compact system is capable of providing magnetic fields greater than 15 kA/m at 150 kHz. That is, the system is relatively compact in that due to the desired orientation of the magnetic field relative to the head, the coil may be placed about the head to have the desired clearances. Thus, it is desirable to have a coil to be shaped approximately as the head such that the magnetic field can be concentrated at the location of the tumor, while also resulting minimal heating in the undesired locations of the head. As such, a circular or oval shaped coil may be used to place the coil about the head and close to the tumor to generate the appropriate magnetic field.

The disclosed coil design has higher magnetic fields compared to known systems that have documented parameters of up to 13.5 kA/m at 100 kHz, and the disclosed system results in substantially lower unintended heating of the patient by eddy currents. That is, the known systems use a design resulting in a flux orientation that is transverse to the disclosed system. Heating of magnetic nanoparticles at low magnetic field strengths tends to be proportional to $H^2f$ (where H is the magnetic field strength and f is the applied frequency), which means that magnetic nanoparticle heating are much higher in the disclosed system, compared to known systems, and in one example may be as much as 85% higher. As field strength rises, the exponent on H declines until the heating rate at a given frequency approaches a threshold value. The value of heating depends upon the specific characteristics of the particle, particle concentration and media, as examples. Therefore, the effective heat deposition for a given magnetic nanoparticle group may be between 50 and 85% higher, compared to known systems.

To treat different known areas, the disclosed induction coil may be adjusted longitudinally up or down relative to the longitudinal axis of the received body, to center the induction coil over the desired treatment area. That is, it is contemplated that the coils disclosed may be used for treating tumor areas that are larger than the approximate area in which the uniform magnetic field occurs, by moving the coil axially during treatment. The same coil on a larger system would be capable of producing substantially larger combinations of magnetic field strength and frequency resulting in higher heating rates. The same coil could also be used with smaller systems for lower levels of field strength and/or frequency.

For the same induction coil geometry, heating of the human body will increase proportional to $H^2f^2$. Issues with patient unintended heating by eddy currents using the transverse flux coil have been reported at the field strength of 13.5 kA/m at 100 kHz, which is what has prevented using higher field strengths in known devices. In one example, a median $T_{90}$ was achieved in a Stage I clinical trial at 40.5 C, and a median CEM43 was 7.7 minutes for a 60 minute treatment.

Other side effects documented for known systems is in the use, for GBM treatment including tachycardia, headaches, elevated blood pressure and focal convulsions. These side effects are highly likely due to poor rectification of the incoming line voltage as these effects are known to occur near line frequency, but not at these field strengths at higher frequencies (>50 kHz).

Higher magnetic field strengths are desirable in order to increase magnetic nanoparticle heating rates, which result in higher tumor/target temperatures. The higher the tumor/target temperature, the more effective the treatment will be. Thus, the disclosed system results in higher field strengths, and will be safe with the disclosed coil known through a combination of computer modeling and experimental testing using a human sized head gel phantom.

Operation of the system, areas of applicability, provided effects, and advantages of the disclosed design will become apparent from the following. It should be understood that the specific examples described below indicate illustrative approaches and are intended for purposes of illustration only and are not intended to limit the scope of the disclosure.

The following description of the illustrative approaches is merely exemplary in nature and is in no way intended to limit the disclosed subject matter, its application, or its uses. To determine the overall size of the induction coil set and the corresponding electrical parameters, calculations for a single turn coil were made using a computer simulation program. Human beings have variation in the properties (overall size and shape, individual organ/tissue sizes, skull thickness, vasculature, conductivity, etc.) that are relevant to magnetic hyperthermia.

To simplify the calculations to demonstrate the advantages of the disclosure, oval dimensions of the head and the coil were converted to equivalent round dimensions. The simulation is then made using an axisymmetric assumption. A cylinder of 20 cm diameter, 20 cm long was used as an approximation. Heat transfer due to convection with a heat transfer coefficient of 10 W/m$^2$ K is assumed on the perimeter of the cylinder, which is a common approximation for natural convection. The human head model is approximated as having a uniform electrical and thermal conductivity. The electrical conductivity used was 0.16 Sm$^{-1}$, which is based upon data from the Air Force Research Lab which listed electrical conductivity at 100 kHz for brain matter between 0.118 and 0.217 in their Radiation Radiofrequency Dosimetry Handbook of 1986. The value used for thermal conductivity for brain tissue in literature is around 0.5 W/mK. Heat transfer in a real or actual human head is quite complex and blood perfusion is a dominant method of heat transfer. Perfusion heat transfer is also highly non-linear with temperature and vastly different for grey and white matter. There is little reliable documentation on this dynamic and it varies from patient to patient. Therefore, for simplicity in the disclosed model, a higher than standard value for thermal conductivity, such as 2.5 W/mK, is used for exemplary purposes and does not include perfusion in the model. The models show qualitative differences in predicted temperatures in the bodies for the different coil length to diameter ratios rather than quantitative values Coil diameter was fixed at 21.2 cm for this disclosure to demonstrate the dynamics.

When properly sized, a single turn coil (whether round or oval) is the optimal configuration for minimizing the reactive and active power in a large, cylindrical volume and minimizing the electrical field strength the patient would be exposed to. The electrical field strength in the leads area is directly proportional to the coil head voltage. The coil head voltage is proportional to the number of turns. The coil head voltage will also be directly proportional to the magnetic field strength and the frequency. Thus, although a single turn coil is an optimal configuration, it is contemplated that coils having more than one turn may be used according to the disclosure. That is, for low magnetic field strengths, it may be desirable to use two or possibly three turns to match the induction coil efficiently to a heat station and power supply. However, to maintain the relatively compact nature of the disclosed coil design and to match to the heat station and power supply, the number of coil turns are appropriately limited and it is not desirable to alter the voltage characteristics by altering the coil length—instead of the number of turns. As will be further illustrated, it is desirable to maintain the length/diameter between 0.25 and 0.75, thus to match the heat station and power supply the number of coil turns may be appropriately selected.

The electrical field strength should be sufficiently low where it is not a significant risk to the patient. The length of the coil was varied between 0.19 and 1 times the equivalent internal diameter of the induction coil to maximize the magnetic field strength in the volume of interest and minimize the unintended heating by eddy currents in the human head. A value of 1 times diameter is an upper limit for the case of GBM, due to the fact that the coil would start to run into the human shoulder at this point. As the coil approaches the shoulders, shielding will become necessary as this region of the body will heat much more efficiently it has a much larger equivalent diameter. The results indicate an optimum occurs between approximately l/d of 0.25 and l/d of 0.75, wherein a tradeoff is made between having an acceptable amount of unintended heating, while providing sufficient magnetic flux to the susceptors of the target region.

Figure 2:
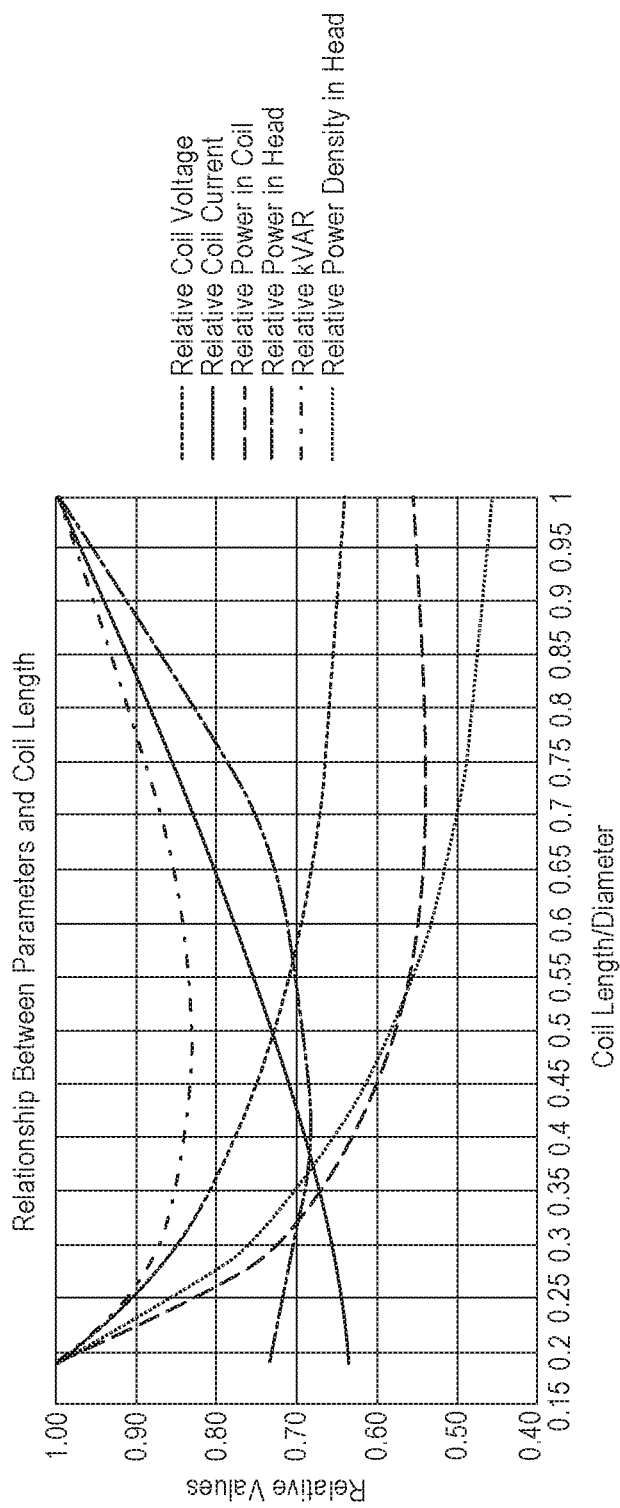
FIG. 2 illustrates the effect of coil length on key system parameters.

FIG. 2 shows how various parameters identified above vary with the coil length to diameter ratio. One parameter: Coil current decreases over the entire range for lower values of length over diameter. However, at very low values, the curve is beginning to flatten out and there are declining benefits of reducing the ratio further. Two parameters: apparent power and power in the head, experience a minimum value between 0.25 and 0.75 length to diameter ratios. Three parameters: Coil voltage, losses in the induction coil and maximum power density in the head are at their minimum values for larger length to diameter values. However, above 0.75 length to diameter ratios there are diminishing returns on further increases in coil length.

As stated above, one important performance determinant is the ability to achieve differential heating in the tumor volume relative to surrounding healthy tissue provided that the electrical parameters are not too large. For GBM, disclosed studies show that due to the smaller size of the human head relative to the torso, these parameters are manageable using an optimized coil with commercially available susceptors (magnetic nanoparticles, thermoseeds, or other metallic inserts) for field strengths that the human body can tolerate without excessive heating by eddy currents. Therefore, two important components related to the length selection to minimize the unintended heating due to eddy currents are total power induced in the head (body) and the maximum power density in the head. One favors short coils and one favors longer coils.

Figure 3:
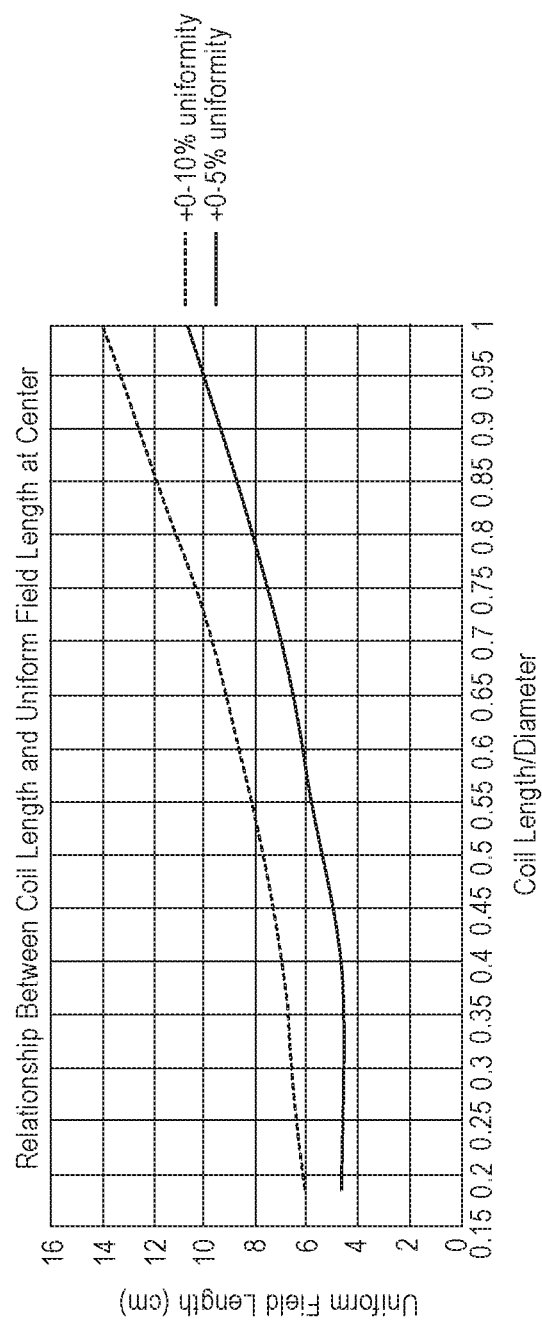
FIG. 3 illustrates the effect of coil length on length of uniform field area at a body centerline for a 21.2 cm diameter coil.

Intended heating is related to the magnetic field strength in the target area. It is desirable to have a relatively uniform distribution of magnetic field strength in the tumor volume to ensure uniform power input. For comparative purposes, a tumor with diameter of 2 cm and length of 4 cm (volume of approximately 10.3 cm$^3$) placed at the center of the head was used in the exemplary models for comparative purposes. This is a typical size for a typical GBM tumor and is one example for tumor location from an electromagnetic and thermal point of view. FIG. 3 shows the length of "uniform" field relative to the length to diameter ratio of the coil, at a body centerline for a 21.2 cm diameter coil. For longer coils, according to an example of the disclosure, a uniform length will grow proportionally to its diameter. All coils considered meet both +0/−5% and +0/−10% uniformity criteria in a length greater than the tumor volume. This means that for the same magnetic field strength in the tumor volume, it can be expected having the same amount of desired heating for all three cases.

To analyze the thermal impact of the coil length on the heating dynamics, the same coils were compared for the case of a magnetic field strength of 7.9 kA/m+/−1.5% at 150 kHz in the tumor. No susceptors were placed in the tumor for additional heating. The exemplary trials were run to temperature distributions in excess of what would be typically tolerable in a human in the exemplary models to make a comparison of the designs, with an understanding that the trends from design to design hold based on different operating parameters. Similar dynamics would occur at different field strengths, only the magnitudes of the variations would be different. For demonstration purposes, length to diameter ratios of 0.19 to infinitely long are discussed in detail below.

Figure 4:
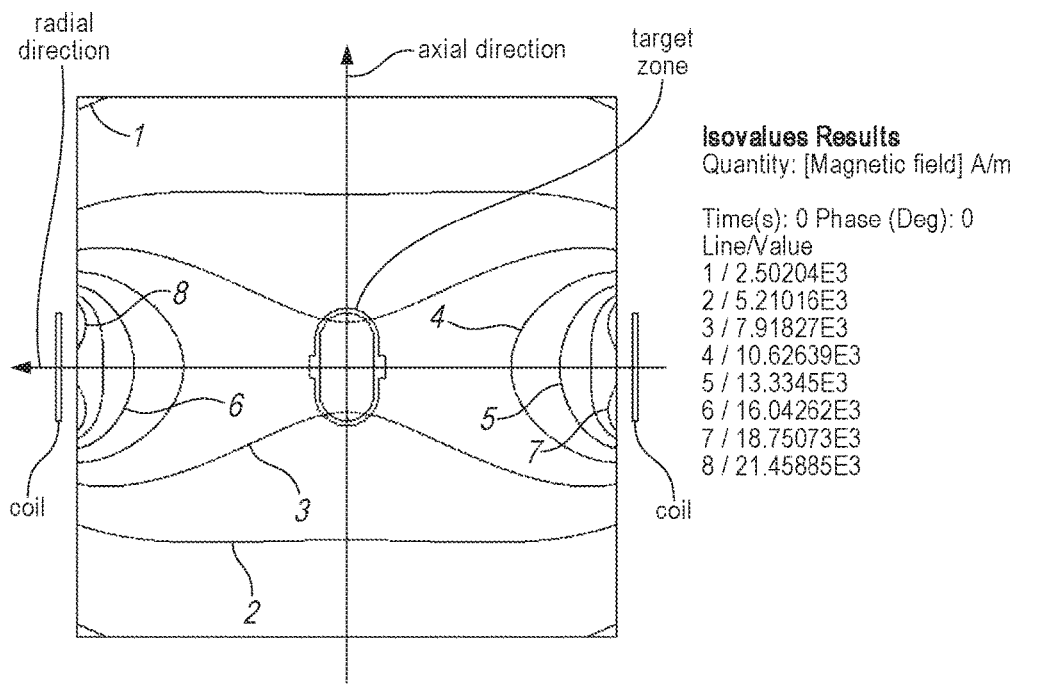
FIG. 4 illustrates a computer simulation of magnetic field strength distribution in a single turn induction coil having a length/diameter of 0.19 using an example of possible treatment of glioblastoma multiforme (GBM) with a model of a human head as an illustration, and represented as a cylinder for modeling purposes.
Figure 5:
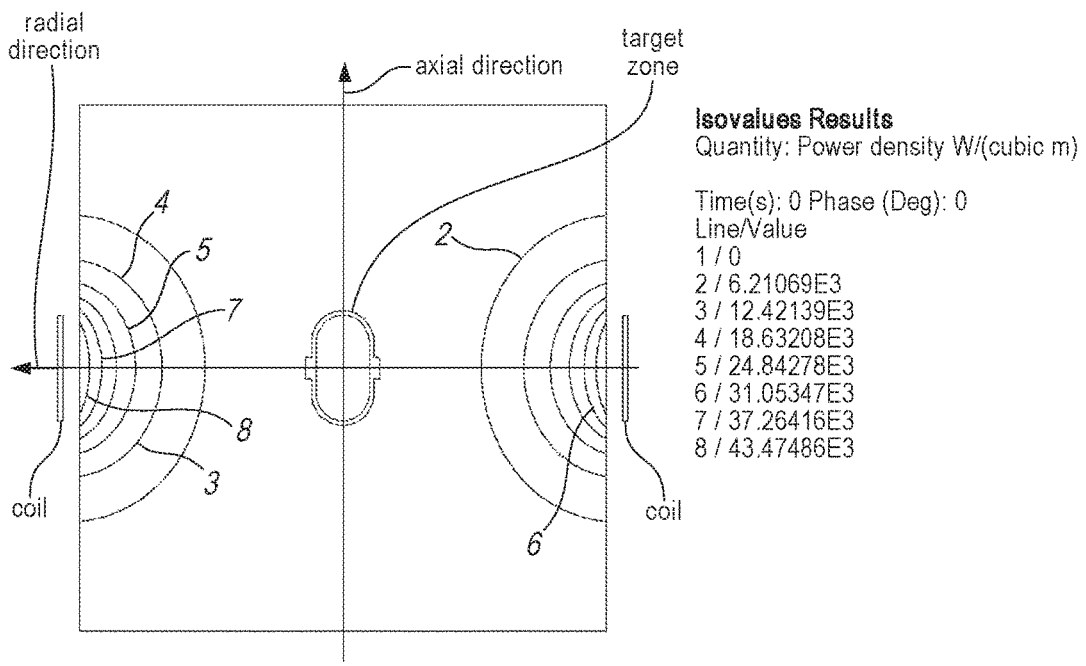
FIG. 5 illustrates a computer simulation power density distribution in a cylinder uniform conductivity of equivalent dimensions to a human head and with conductivity equal to that of human brain tissue in a single turn coil and a length/diameter of 0.19.

Distribution of magnetic field strength in a cylindrical area is shown in FIG. 4 for a coil with length of approximately 0.19 times the diameter. For this ratio, the radial field strength gradients are very large, meaning potential variation in magnetic field strength for tumors not located in the center of the brain. This means that there may be a radial gradient in the field strength in the tumors in this instance. This could be compensated for by the physician skilled in the art by varying the susceptor concentration based upon radial location in a tumor of known location. These gradients (along with coil tuning) are one of the reasons that others have shied away from this area of coil design. The general desire was to have a relatively large zone of uniform field capable of treating a tumor anywhere in the volume of interest. However, with modern imaging techniques, this would be an advantage for large numbers of small tumors, such as metastases, but which are not currently considered candidates for treatment by the above methods (except in the case of mild hyperthermia of a whole region of tissue, which would be combined with another complimentary treatment, such as radiation). This feature would actually be an advantage for tumors not located in the geometrical center of the body of interest to a physician skilled in the art, as it would mean higher heating rates in tumors with susceptors inserted due to the higher magnetic field strengths relative to the surrounding healthy tissue. Also, near the outside diameter of the body, the field strength maxima are located near the coil ends, rather than in the center. This was also cautionary, as the formula for induced power in a body is proportional to H$^2$. However, because the body diameter is substantially lower than the electrical reference depth, this does not hold. What is more important is the value of H throughout the given cross-section, which is lower than in the center due to divergence of field due to the coil end effect. The associated power density in the simplified head is shown in FIG. 5. The band is relatively narrow, but unlike the field strength the maximum value is on the centerline due to the above consideration. Modeled properties are not temperature dependent, so the distribution of power density will be constant throughout the theoretical cycles.

Figure 6:
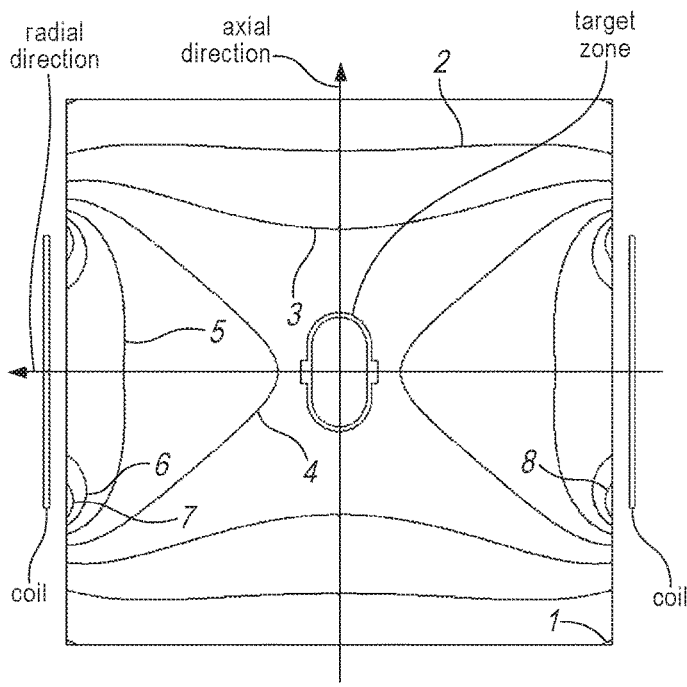
FIG. 6 illustrates a computer simulation of magnetic field strength distribution in a single turn induction coil having a length/diameter of 0.47 using an example of possible treatment of glioblastoma multiforme (GBM) with a model of a human head as an illustration, and represented as a cylinder for modeling purposes.

Distribution of magnetic field strength in a cylindrical area is shown in FIG. 6 for a coil with length of approximately 0.47 times the diameter. For this ratio, the radial field strength gradients are substantially smaller than for the 0.19

Figure 7:
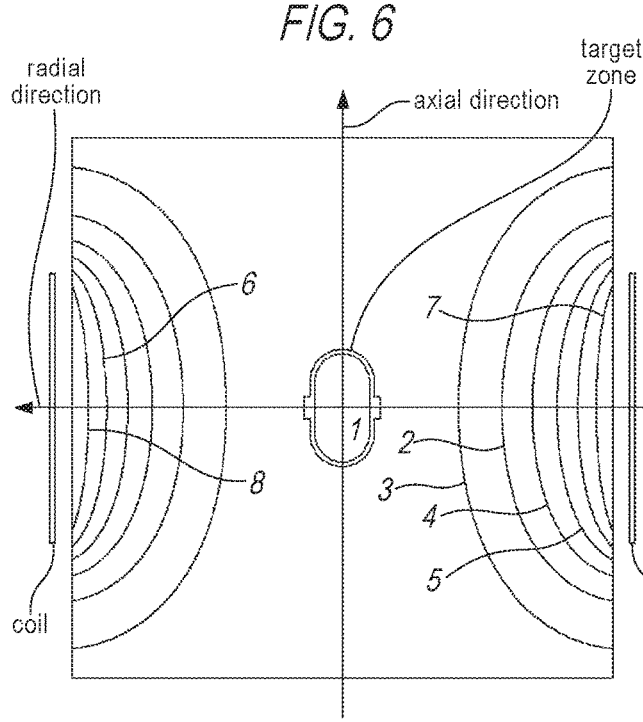
FIG. 7 illustrates a computer simulation power density distribution in a cylinder uniform conductivity of equivalent dimensions to a human head and with conductivity equal to that of human brain tissue in a single turn coil and a length/diameter of 0.47.

L/D ratio, meaning less sensitivity for treating tumors not located in the center of the brain, therefore smaller differential in susceptor loading is desired. Again, near the outside diameter of the body, the field strength maxima are located near the coil ends, rather than in the center. The associated power density in the simplified head is shown in FIG. 7. The band is substantially wider than for the 0.19 L/D ratio and the maximum value is on the centerline. The maximum value of power density is also substantially lower than for the 0.19 L/D ratio.

Figure 8:
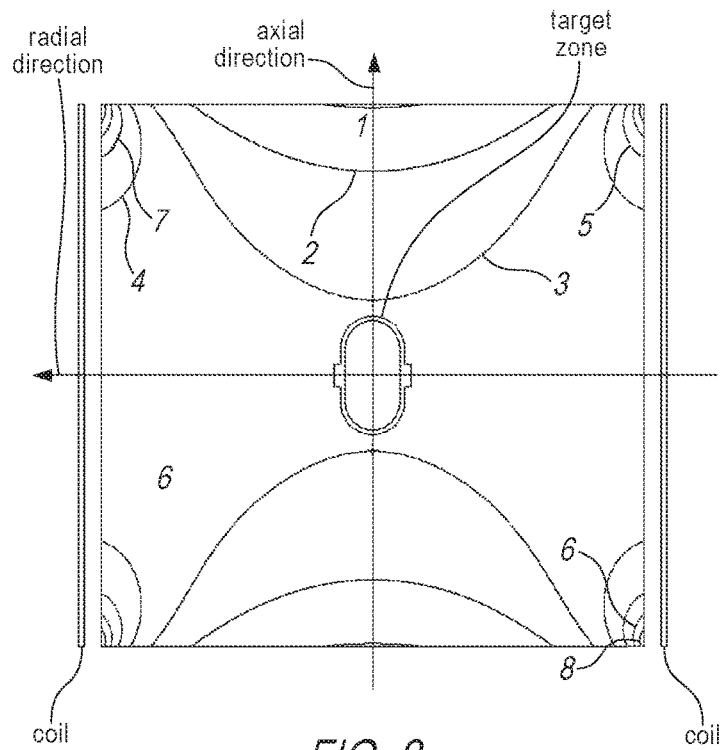
FIG. 8 illustrates a computer simulation of magnetic field strength distribution in a cylindrical shape for a coil with length of approximately 0.94 times the diameter.
Figure 9:
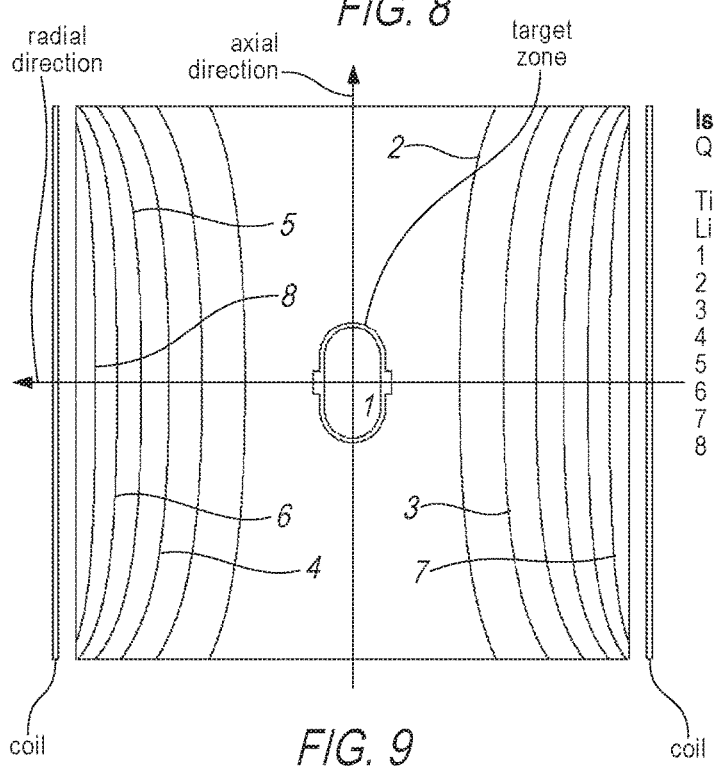
FIG. 9 illustrates an associated power density in a simplified head for a coil with length of approximately 0.94 times the diameter.

Distribution of magnetic field strength in a cylindrical area is shown in FIG. 8 for a coil with length of approximately 0.94 times the diameter. For this ratio, the radial field strength gradients are quite small. This coil will be very tolerant to tumor positioning and will typically not need any special pre-treatment planning to compensate for tumor location due to magnetic field variation within the tumor. Again, near the outside diameter of the body, the field strength maxima are located near the coil ends, rather than in the center. The associated power density in the simplified head is shown in FIG. 9. The band is now almost as long as the head is and there is a relatively small variation in length. There reduction in maximum power density compared to the 0.47 L/D coil is less than the increase in the length of the heated zone.

Figure 10:
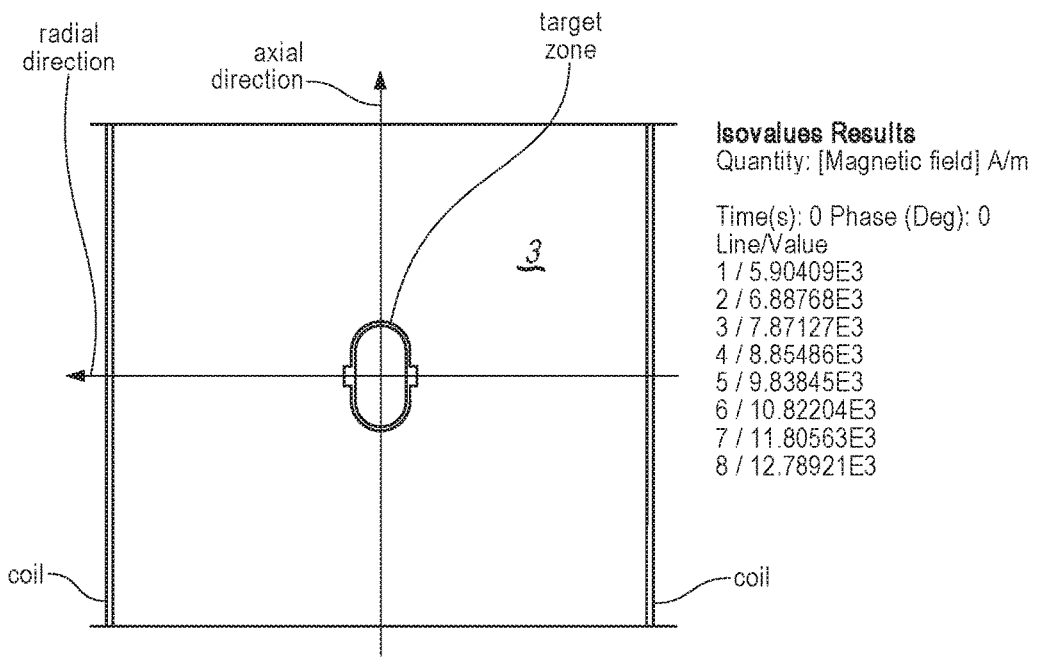
FIG. 10 illustrates a computer simulation of magnetic field strength distribution in a single turn induction coil having a length/diameter of infinity using an example of possible treatment of glioblastoma multiforme (GBM) with a model of a human head as an illustration, and represented as a cylinder for modeling purposes.
Figure 11:
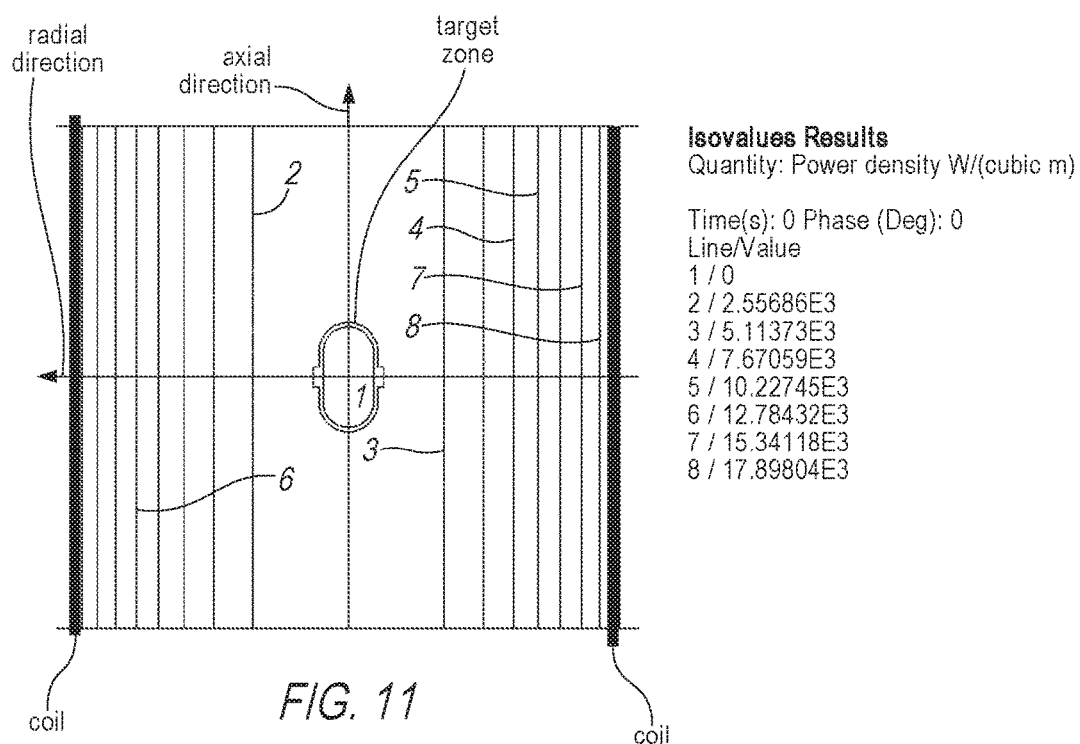
FIG. 11 illustrates a computer simulation power density distribution in a cylinder uniform conductivity of equivalent dimensions to a human head and with conductivity equal to that of human brain tissue in a single turn coil and a length/diameter of infinity.

Distribution of magnetic field strength in the head area is shown in FIG. 10 for a coil with (theoretically) infinite coil length. For this ratio, the radial and axial field strength gradients are zero. And, for this scenario the magnetic field is approximately 7.9E3 A/m, represented by item 3 of the corresponding results, a '3' being positioned within the field as shown in FIG. 10. The associated power density in the simplified head is shown in FIG. 11. The power density now has no variation in length in this theoretical illustration. There, reduction in maximum power density compared to the 0.94 L/D coil is quite small.

Each of FIGS. 4-15 shows an oblong symbol at the center that is labeled as a "target zone", and each of FIGS. 4-15 illustrates an "axial direction" and a "radial direction". The "radial direction" corresponds with radial direction 114 shown in FIGS. 1B and 1C, and the axial direction corresponds with axial direction 112 in FIG. 1B. Each of FIGS. 4-15 also shows a "coil" on either side of the simulation area, which is reflected through the vertical arrow within the results that is labeled as "axial direction", therefore approximated as a cylindrical shape. In addition, simulation results are shown of magnetic field, power distribution, and temperature in a cylindrical volume of uniform conductivity, which is used to approximate temperatures that would occur in a human head.

Figure 12:
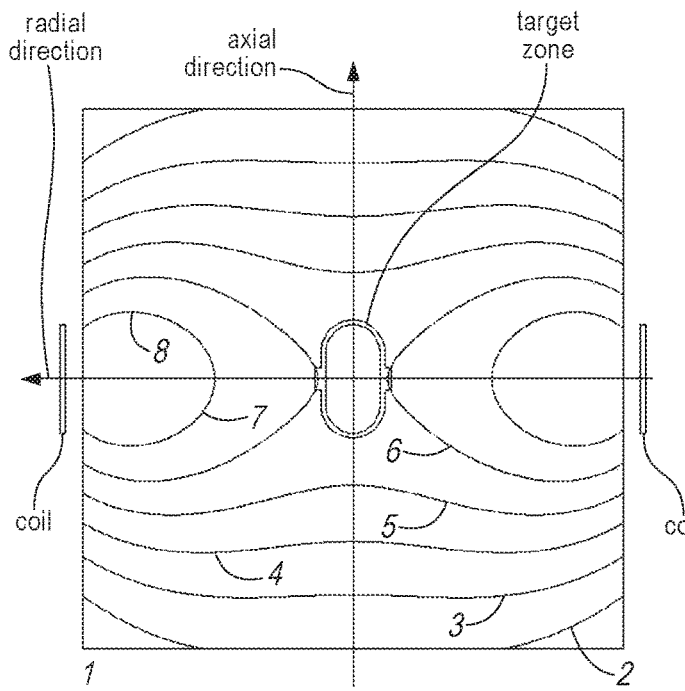
FIG. 12 illustrates temperature distribution at for a long thermal cycle for the 0.19 length to diameter coils.
Figure 13:
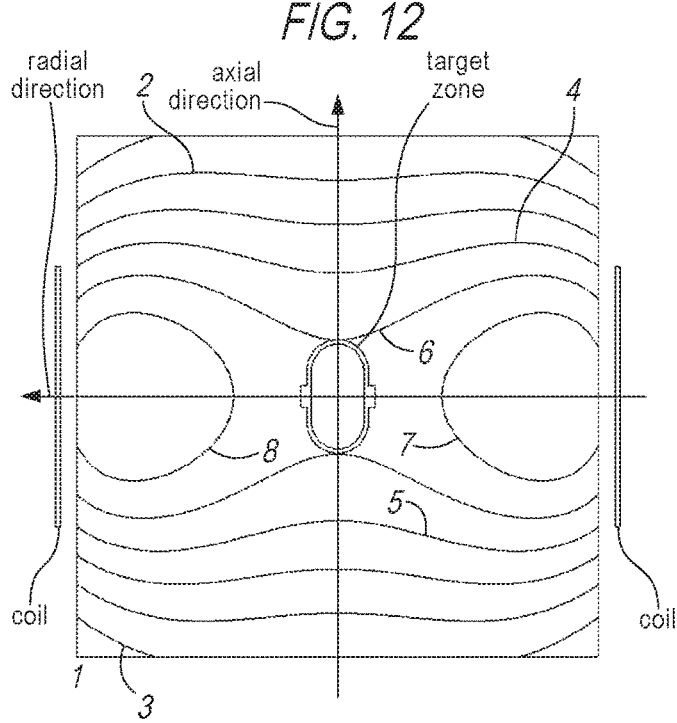
FIG. 13 illustrates temperature distribution at for a long thermal cycle for the 0.47 length to diameter coils.
Figure 14:
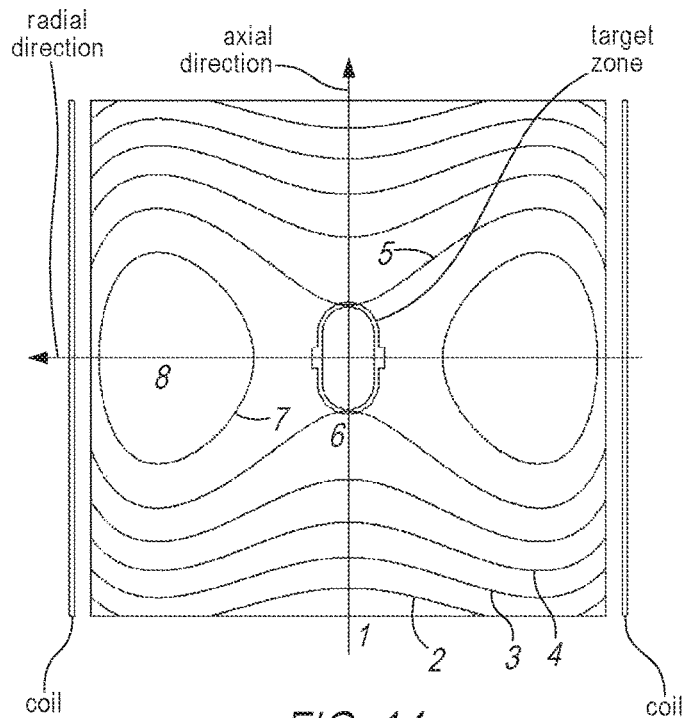
FIG. 14 illustrates temperature distribution at for a long thermal cycle for the 0.94 length to diameter coils.
Figure 15:
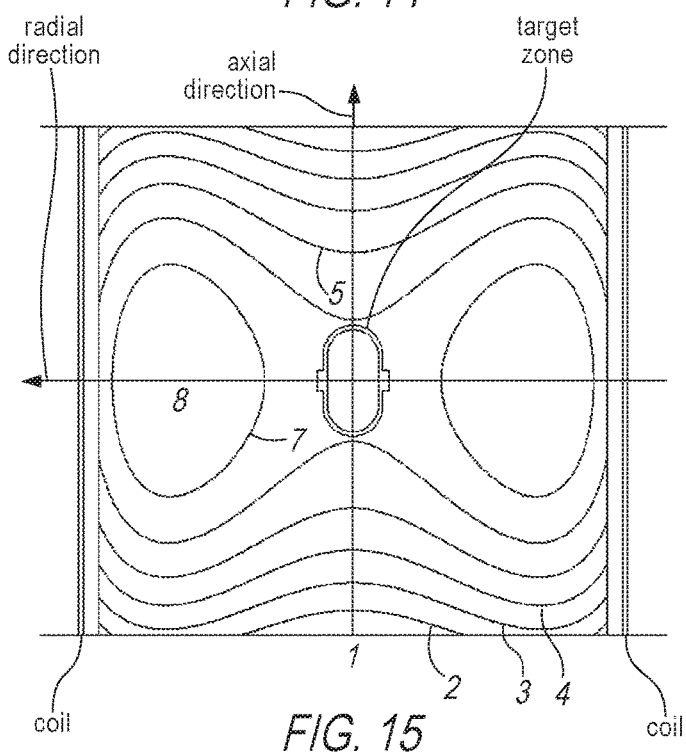
FIG. 15 illustrates temperature distribution at for a long thermal cycle for the infinite length to diameter coils.

The coil in FIGS. 4, 5, and 12 corresponds to the length/diameter of 0.19, the coil of FIGS. 6, 7, and 13 corresponds to the longer length/diameter of 0.47, the coil of FIGS. 8, 9, and 14 corresponds to the length/diameter of 0.94, and the coil of FIGS. 10, 11, and 15 corresponds to an infinitely long coil (the lengths along the axial directions are shown, accordingly and correspondingly). Although the heating is in fact dynamic and the temperatures and temperature distributions generally change over time, a snapshot in time in each of the temperature figures (FIG. 12, FIG. 13, FIG. 14 and FIG. 15 is shown for a long cycle (long cycles are generally popular for hyperthermia to increase the CEM 43 value and increase treatment efficacy, and a "long" thermal cycle is generally considered for the purposes of this disclosure to be 10's to 100's of minutes in length) illustrates the amount of heating that will occur but without any effect of susceptors with the same temperature scale (omitted as it is only for exemplary purposes). That is, each of FIGS. 12 (0.19 L/D), 13 (0.47 L/D), 14 (0.94 L/D) and 15 (infinitely long) shows a temperature profile that would occur in each of the target zones if there are no susceptors present. As such, FIGS. 12-15 illustrate the amount of heating that occurs, clearly indicating that the amount of unintentional heating surrounding the target zones can be kept to a relative minimum. Thus, with the application of the magnetic field as indicated in each of FIGS. 4, 6, 8 and 10, the amount of intentional heating can thus be limited to the target zone with the proper delivery of susceptors to the target zone, while the healthy tissue immediately surrounding the target zone experiences relatively little unintentional heating.

The longer coils produce substantially larger zones of uniform field, power density and temperature. The maximum values of power density and magnetic field strength in the head (same value in tumor) are significantly higher for the shorter coils. However, the minimum value of temperature in the healthy tissue occurs in the 0.47 L/D coil. This is because at this field strength with this size body, the difference in power density is outweighed by the heat transfer within the body. For the shortest coil considered, 0.19 L/D, the maximum temperature rises as the difference in power density is stronger than heat transfer in the disclosed model numbers. For all cases, the maximum temperature is at the centerline at a radius of approximately 8 cm due to the balance between induced power and heat transfer within the system.

Figure 16:
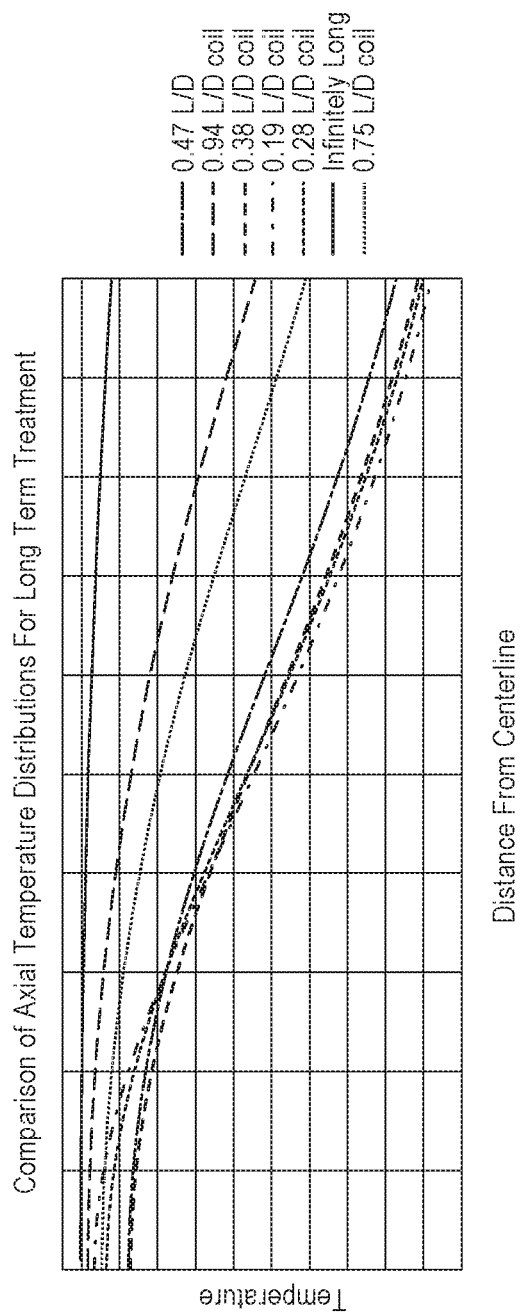
FIG. 16 illustrates temperature dynamics at 8 cm radius in the centerline of the head (approximate location of maximum temperature) versus time for length to diameter (l/d) ratios of 0.19 (4 cm), 0.28 (6 cm), 0.38 (8 cm), 0.47 (10 cm), 0.75 (16 cm), 0.94 (20 cm) and infinitely long for a long thermal cycle (generally considered, for the purposes of this disclosure, to be 10's to 100's of minutes in length).

FIG. 16 is an exemplary illustration showing trends of temperature distributions for different length to diameter ratios between 0.19 and infinity. That is, FIG. 16 illustrates a series of exemplary and hypothetical temperature profiles that occur about coil center 118 of FIG. 1B and along the axial direction 112 thereof. The profiles occur also at a hypothetical long heating cycle, shown to illustrate the general trends of the disclosed system. Different temperature profiles result from different length/diameter (l/d) ratios.

The "shortest" and "longest" coils produce the highest maximum temperatures. The "longer" coils could be considered to produce the worst temperature distributions, because a much larger portion of the head would be exposed to elevated temperatures. The minimum of the maximum temperatures that occur are in the range of 0.25 to 0.75 L/D ratios. Generally, the most favorable temperature distributions occurs for the 0.38 L/D ratio for this case. This value may vary somewhat depending upon the physical properties, the proposed treatment cycle and the location of the tumor and distance from the body to the surface of the induction coil.

In general, it is contemplated that unintended heating within the brain should not exceed a maximum value, shown as maximum temperature 202 in FIG. 15. In one example, it is desirable that the maximum temperature does not exceed 43° C., however, it is contemplated that other maximum temperatures may be considered for other applications.

The various temperature distributions occur at the illustrated hypothetical snapshot in time for l/d ratios: 0.19; 0.28; 0.38; 0.47; 0.75; 0.94; and ~∞. As can be seen, for a short l/d, peak temperatures occur compared to other l/d profiles, and in fact may exceed a maximum desirable temperature. At another extreme is for a hypothetical limit where l/d equals ~∞ (i.e., infinity). At this hypothetical extreme the temperature profile remains fairly uniform throughout a target area and at a generally higher value. As such, an optimum occurs between approximately l/d of 0.25 and l/d of 0.75, wherein a tradeoff is made between having an acceptable amount of unintended heating, while providing sufficient magnetic flux to the susceptors of the target region. For tumors closer to the surface, due to the radial gradient of the field, this will tend to increase the advantages of going to a coil on the lower end of the range. In one example an optimum ratio of the length to the effective diameter is above 0.38, and in one example an optimal performance occurs with power supply 104 having and input frequency that ranges between 100 kHz and 300 kHz. Thus, for a coil having a l/d that is less than 0.25, FIG. 15 indicates that excessive heating may occur above the maximum temperature, which can lead to damage of healthy tissue, while providing a sharp drop off outside of the target zone. At the other extreme, a flat temperature profile occurs at the hypothetical limit of l/d~∞, resulting in a flat temperature profile that produces the highest maximum temperature.

Therefore, the optimal length of a coil for GBM lies between 0.25 and 0.75 l/d, depending upon the treatment cycle, which provides sufficient magnetic field to the target zone, while also providing an acceptable amount of unintended heating outside the target zone.

A disclosed method of treating a tumor in a human brain therefore includes positioning an induction coil over the human head, the induction coil having a ratio of a length to an effective diameter that ranges between 0.25 and 0.75, and applying an input frequency between 50 kHz and 1 MHz to the induction coil between 50 kHz and such that a magnetic field is generated that ranges between 1 kA/m and 40 kA/m. The effective diameter is determined based on a cross-sectional area of the induction coil, and the length is determined along an axis of the induction coil that is orthogonal to the cross-sectional area.

What is claimed is:

1. An induction coil for heating susceptors within a portion of a living body, comprising:
   an effective diameter that is determined based on a cross-sectional area of the induction coil;
   a length determined along an axis of the induction coil that is orthogonal to the cross-sectional area; and
   a ratio of the length to the effective diameter that ranges between 0.25 and 0.75, such that a magnetic field is generated that ranges between 1 kA/m and 40 kA/m with an input frequency that ranges between 50 kHz and 1 MHz.

2. The induction coil of claim 1, wherein the coil is shaped as one of an oval and a circle.

3. The induction coil of claim 1, wherein the effective diameter is a square root of four times a ratio of the cross-sectional area divided by $\pi$.

4. The induction coil of claim 1, wherein the coil is a single turn coil.

5. The induction coil of claim 1, wherein the coil includes two or three turns.

6. The induction coil of claim 1, wherein the portion of the living body is a human head.

7. The induction coil of claim 1, wherein the coil includes a cross-sectional area that is sufficient to pass over a human head containing the susceptors such that the human head is positionable along the axis of the induction coil.

8. The induction coil of claim 1, wherein the input frequency ranges between 50 kHz and 200 kHz.

9. A method of heating susceptors within a living body, comprising:
   positioning an induction coil over a portion of a living body containing susceptors, the induction coil having a ratio of a length to an effective diameter that ranges between 0.25 and 0.75; and
   applying an input frequency between 50 kHz and 1 MHz to the induction coil such that a magnetic field is generated that ranges between 1 kA/m and 40 kA/m;
   wherein the effective diameter is determined based on a cross-sectional area of the induction coil, and the length is determined along an axis of the induction coil that is orthogonal to the cross-sectional area.

10. The method of claim 9, further comprising magnetic nanoparticles as the susceptors, and delivering the magnetic nanoparticles to a tumor by one of direct injection and an antibody guide.

11. The method of claim 9, wherein the coil is shaped as one of an oval and a circle.

12. The method of claim 9, wherein the effective diameter is determined as a square root of the cross-sectional area divided by $\pi$.

13. The method of claim 9, wherein the coil is a single turn coil.

14. The method of claim 9, wherein the coil includes two or three turns.

15. The method of claim 9, wherein the portion of the living body is a human head.

16. The method of claim 9, wherein applying the input frequency comprises applying the input frequency between 50 kHz and 200 kHz.

17. A system for applying a magnetic field to a human head, comprising:
   a power supply configured to output an AC power having a frequency between at least 50 kHz and 1 MHz;
   a coil coupled to an output of the power supply, the coil comprising:
      a cross-sectional area sufficient to pass over the human head such that the human head is positionable along an axis of the coil, the coil having an effective diameter that is determined based on a cross-sectional area of the induction coil;
      a length determined along the axis of the induction coil that is orthogonal to the cross-sectional area; and
      a ratio of the length to the effective diameter that ranges between 0.25 and 0.75, such that a magnetic field is generated that ranges between 1 kA/m and 40 kA/m with an input frequency that ranges between 50 kHz and 1 MHz.

18. The system of claim 17, wherein the coil is shaped as one of an oval and a circle.

19. The system of claim 17, wherein the effective diameter is two times a square root of a ratio of the cross-sectional area divided by $\pi$.

20. The system of claim 17, wherein the coil is a single turn coil.

* * * * *